United States Patent [19]

Hagler

[11] Patent Number: 4,918,941
[45] Date of Patent: Apr. 24, 1990

[54] CRYOGENIC ULTRAMICROTOME SEAL

[75] Inventor: Herbert K. Hagler, Dallas, Tex.

[73] Assignee: Board of Regents, The University of Texas System, Austin, Tex.

[21] Appl. No.: 353,804

[22] Filed: May 16, 1989

[51] Int. Cl.⁵ ............................................. F25C 5/02
[52] U.S. Cl. ..................................... 62/320; 83/171; 83/915.5
[58] Field of Search ................... 62/320; 83/170, 171, 83/915.5

[56] References Cited

U.S. PATENT DOCUMENTS

| | | | |
|---|---|---|---|
| 3,204,424 | 9/1965 | McCormack et al. | 62/320 |
| 3,218,896 | 11/1965 | McCormick | 83/15 |
| 3,236,133 | 2/1966 | DePas | 83/915.5 |
| 3,351,396 | 11/1967 | Oechslin | 308/36.3 |
| 3,447,594 | 6/1969 | Andrews | 165/2 |
| 3,495,490 | 2/1970 | Dollhopf | 83/171 |
| 3,701,536 | 10/1972 | Matthews et al. | 277/56 |
| 3,828,571 | 8/1974 | Lechner | 62/320 |
| 4,278,263 | 7/1981 | Rosen | 83/915.5 |
| 4,290,610 | 9/1981 | Lizogub et al. | 277/13 |

OTHER PUBLICATIONS

R. H. Warring, "Seals and Sealing Handbook," Gulf Publishing Company, 1981, pp. 282-284, 297-299, 345-350.

Antionio Artiles, Wilber Shapiro and Henry F. Jones, "Design Analysis of Rayleigh-Step Floating-Ring Seals," ASLE Transactions, vol. 27, Jul. 4, 1983, pp. 321-331.

R. Hamm and W. Shapiro, "Testing of Helium-Buffered, Rayleigh-Step, Floating-Ring Seals," Lubrication Engineering, May 1987, pp. 376-383.

Primary Examiner—Ronald C. Capossela
Attorney, Agent, or Firm—Arnold, White & Durkee

[57] ABSTRACT

A cryogenic seal, and a cryogenic ultramicrotome using the seal are presented. The seal allows a microtome arm to pass through an aperture in the wall of a cryogenic microtome chamber providing thermal insulation while allowing manipulation of the microtome arm within the chamber. The seal includes a thermally conductive seal container having a number of thermally insulating baffle inserts therein. The baffle inserts are placed within the seal container to form a plurality of baffle chambers, and each baffle insert includes an aperture which is larger in circumference than the external circumference of the microtome arm. Within each baffle chamber is a baffle membrane, each membrane having an aperture through which the microtome arm passes in sliding contact. The baffle inserts and baffle membranes together form a thermally insulating labyrinth seal between the interior and the exterior of the cryogenic chamber, and allow the microtome arm to be easily and accurately manipulated from the exterior of the chamber.

15 Claims, 3 Drawing Sheets

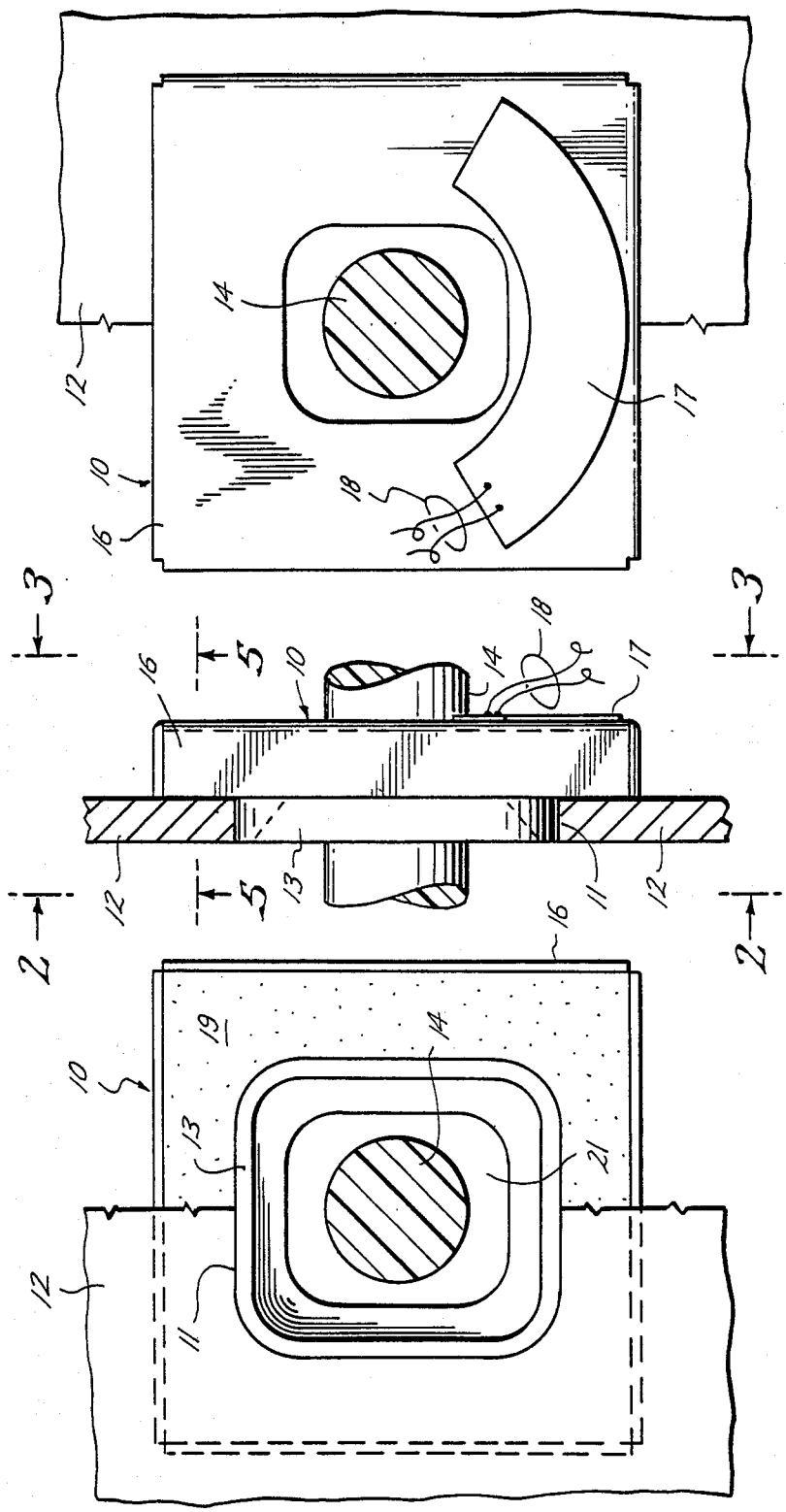

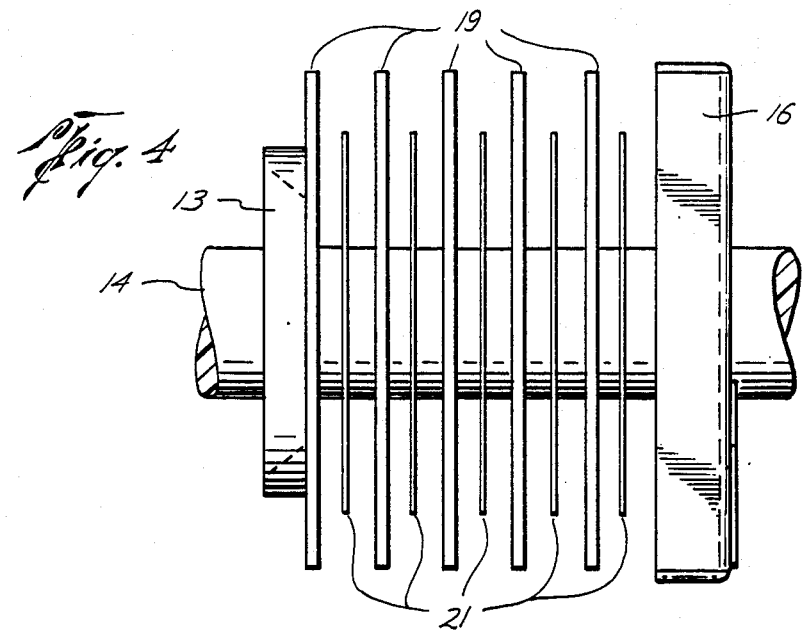
Fig. 4
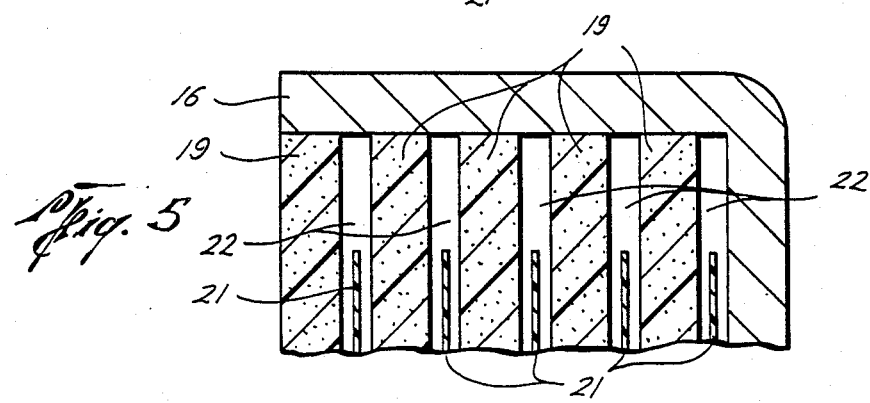
Fig. 5
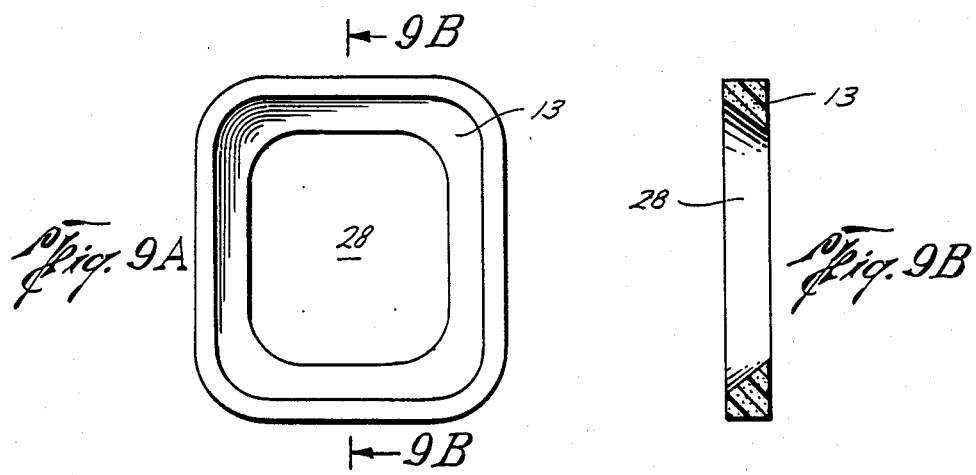
Fig. 9A
Fig. 9B

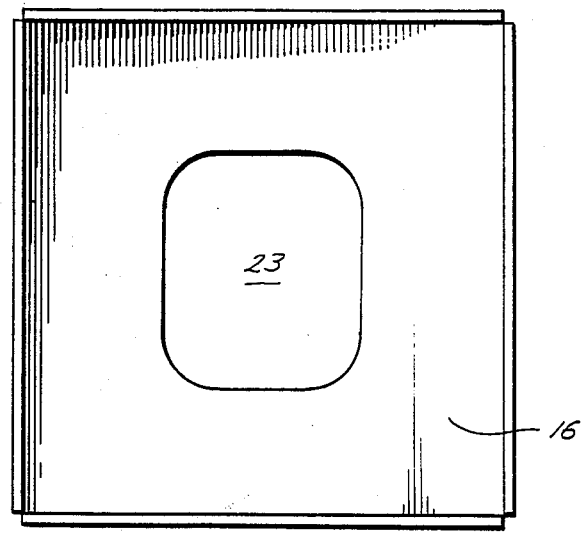
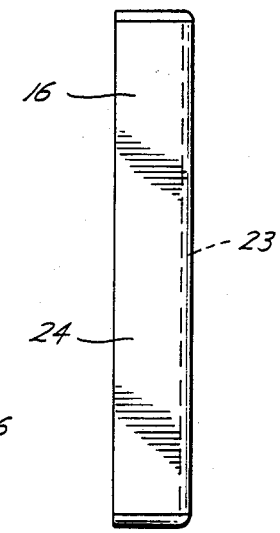
Fig. 6A        Fig. 6B
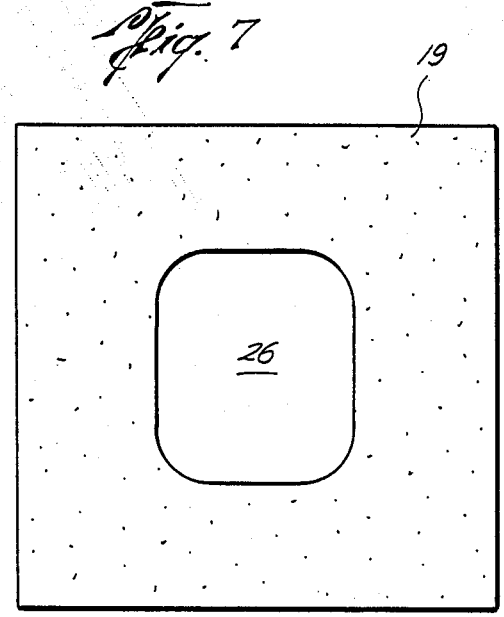
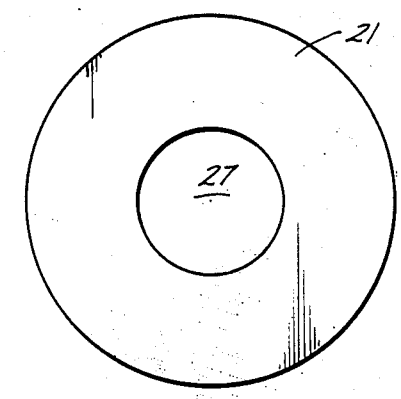
Fig. 7        Fig. 8

CRYOGENIC ULTRAMICROTOME SEAL

BACKGROUND OF THE INVENTION

The invention relates to thermally insulating cryogenic ultramicrotome seals.

Cryogenic microtomes and ultramicrotomes generally include an enclosed cryogenic chamber which is cooled by a cryogenic liquid coolant, such as liquid nitrogen, to control the interior of the cryogenic chamber to as low as −196° C. Within the cryogenic chamber are typically located a knife holder and a specimen holder which are moveable relative to one another to produce ultrathin slices of the frozen specimen. Such a known structure can be found in U.S. Pat. No. 3,828,571, the disclosure of which is expressly incorporated herein by reference. These ultrathin samples are necessary for examination of the specimen with, for example, an electron microscope.

Relative movement between the knife and the frozen specimen within the microtome cryogenic chamber can be accomplished by mounting the knife or specimen or both on microtome arms which extend through holes in the cryogenic chamber to the exterior of the chamber where the arms can be manipulated at room temperature. When such microtome arms pass through apertures in the cryogenic chamber, a thermally insulating seal is desirable in order to minimize evaporation of cryogenic liquid contained within the cryogenic chamber and to minimize thermal gradients within the cryogenic chamber which may deleteriously affect the temperature stability of the frozen specimen or knife, or both. At the same time, such a cryogenic seal must not interfere excessively with the precise movement of the microtome arm.

SUMMARY OF THE INVENTION

The present invention is a seal for use in a cryogenic microtome which allows a microtome arm to pass from the interior to the exterior of the cryogenic chamber, thereby providing a thermally insulating seal without excessive interference with precise movement of the microtome arm.

The seal has a labyrinth form and includes a seal container with a plurality of baffle inserts therein, substantially fixed relative to the container. Each of the baffle inserts has an aperture which is substantially aligned with the aperture in the cryogenic chamber and which has a perimeter which is greater than the perimeter of the microtome arm. The baffle inserts are spaced apart to define a plurality of baffle chambers within the seal container. Contained and moveable within each baffle chamber is a baffle membrane through which the microtome arm passes in sliding contact. Fixed to the seal container is a baffle wall plug which has a periphery configured for press fitting within the aperture of the cryogenic chamber, thereby allowing the cryogenic seal surrounding the microtome arm to be attached to the cryogenic chamber. The baffle inserts and baffle membranes together form a thermally insulating labyrinth seal between the interior and exterior of the cryogenic chamber. The movement of the baffle membranes within the baffle chambers formed by the baffle inserts combined with the sliding engagement between the baffle membranes and the microtome arm, allow relatively unimpeded manipulation of the microtome arm from the exterior of the cryogenic chamber.

The baffle inserts, baffle membranes and cryogenic arm are preferably of thermally insulating material, while the seal container is preferably thermally conductive. The baffle membranes can be constructed of, or coated with, anti-static material in order to eliminate the deleterious effects of static electricity within the seal. A low wattage heater can be attached to the exterior of the seal chamber which serves to maintain the interior of the seal in a relatively frost-free condition further promoting ease of manipulation of the microtome arm passing therethrough.

BRIEF DESCRIPTION OF THE DRAWINGS

FIG. 1 is an exterior view of the cryogenic microtome seal of the present invention.
FIG. 2 is a view taken from section 2—2 of FIG. 1.
FIG. 3 is a view taken from section 3—3 of FIG. 1.
FIG. 4 is an exploded view of the cryogenic microtome seal of the present invention.
FIG. 5 is a view taken through section 5—5 of FIG. 1.
FIGS. 6A and 6B are views of the seal container used in the present invention.
FIG. 7 is a baffle insert used in the present invention.
FIG. 8 is a baffle membrane used in the present invention.
FIGS. 9A and 9B are views of a baffle wall plug used in the present invention.

DETAILED DESCRIPTION OF THE PREFERRED EMBODIMENT

Referring to FIGS. 1-3, the cryogenic microtome seal 10 of the present invention is shown in place within aperture 11 of cryogenic chamber 12. In FIG. 1, the low temperature interior of chamber 12 is to the left and the room temperature exterior of chamber 12 is to the right.

Seal 10 is attached to chamber 12 by use of baffle wall plug 13 which is press fitted or otherwise attached within cryogenic chamber aperture 11. The exterior periphery of baffle wall plug 13 is configured to be complementary in shape to the interior periphery of cryogenic chamber aperture 11. Passing through seal 10 from the interior to the exterior of chamber 12 is microtome arm 14 which is preferably constructed of thermally insulating material, for example KEL-F 81 brand plastic material, available from 3M Corporation.

Seal 10 is enclosed within seal container 16 which is preferably constructed from thermally conductive material such as aluminum, copper, or brass. Attached to the exterior of container 16 is low wattage electrical heating element 17 which is connected to a suitable source of electrical power (not shown) by leads 18. Heater 17 serves to maintain the interior of seal 10 in a defrosted condition thereby facilitating the manipulation of microtome arm 14.

Contained within seal container 16 are baffle inserts 19 and baffle membranes 21, the placement of which will be explained in more detail below with respect to FIGS. 4 and 5. Within the interior of cryogenic chamber 12, microtome arm 14 can be used in a manner well known to those skilled in the art to support and manipulate a frozen specimen or a microtome knife.

Referring to FIG. 4, which is an exploded view of the present invention, within seal container 16 are a plurality of baffle inserts 19 interspaced with a plurality of baffle membranes 21. Baffle inserts 19 are configured to be press fitted within the interior of seal container 16 and, when assembled, are substantially fixed relative to seal container 16. Baffle wall plug 13 is affixed, by use of an appropriate adhesive, thermal bonding, or the like, to the left-most baffle 19. Baffle membranes 21 are slidably mounted on microtome arm 14 and are moveable relative to baffle inserts 19 and seal container 16. A section of the interior of cryogenic seal 10 is shown in FIG. 5 which is a view taken through section 5—5 of FIG. 1. Individual baffle inserts 19 are press fitted in spaced apart relationship within seal container 16 to form baffle chambers 22. Baffle inserts 19 are moveable within baffle chambers 22 between baffle inserts 19. Three to five pairs of inserts 19 and membranes 21 have proven acceptable, however any number can be used.

FIGS. 6A and 6B are views of seal container 16. Container 16 is preferably thermally conductive and can be stamped aluminum which is then anodized to prevent surface corrosion. Container 16 has a central aperture 23 which is large enough to accommodate microtome arm 14 (see also FIG. 3) without contact. Seal container 16 is formed with side walls 24. Other suitable materials for container 16 include copper or brass, although other thermally conductive materials are also suitable.

Referring now to FIG. 7, baffle insert 19 is shown. The periphery of baffle insert 19 is configured to fit snugly within the interior of seal container 16 and when assembled, individual baffles 19 are preferably substantially fixed relative to seal container 16. Baffle inserts 19 include an aperture 25 therein through which microtome arm 14 passes without contact when baffle inserts 19 are assembled as shown in FIG. 4. Baffle inserts 19 are preferably thermally insulating and can be made from a closed cell material with a smooth surface such as polystyrene sheet, although other thermally insulating materials are acceptable.

Referring to FIG. 8, the details of baffle membrane 21 are shown. Baffle membrane 21 includes aperture 27 therein which is dimensioned to engage microtome arm 14 (see also FIG. 3) with sliding contact. Aperture 27 is configured to be complementary in shape to the periphery of the cross-section of microtome arm 14. A circular shape is preferred but other geometric shapes are also acceptable. Baffle membrane 21 is constructed of a thermally insulating material and is preferably antistatic. Suitable materials include anti-static treated mylar, mylar coated with anti-static material such as iron oxide, or functionally equivalent structures.

Finally, with reference to FIGS. 9A and 9B, baffle wall plug 13 is shown. Baffle wall plug 13 includes aperture 28 therein through which microtome arm 14 passes without contact when seal 10 is assembled (see also FIG. 2). The outer periphery of baffle wall plug 13 is configured to be press fitted within aperture 11 of cryogenic chamber 12 (see also FIGS. 1 and 2). Baffle wall plug 13 is preferably made from a closed cell plastic foam material such a polystyrene or polyurethane.

While the present invention has been described with reference to a single preferred embodiment, one of ordinary skill in the cryogenic microtome art will understand that modifications, additions or deletions to the invention can be made, without departing from the spirit and scope of the claimed invention.

What is claimed is:

1. A thermal seal for use in a cryogenic ultramicrotome having a cryogenic chamber and a microtome arm extending through an aperture in said cryogenic chamber from a reactively high temperature exterior of said chamber to a relatively low temperature interior of said chamber, said seal comprising:

a seal container attached to said cryogenic chamber;

a plurality of thermally insulating baffle inserts within said container together forming a plurality of baffle chambers, each baffle insert having an aperture therein substantially aligned with said aperture of said cryogenic chamber and being larger than an exterior dimension of a cross-section of said microtome arm; and a plurality of thermally insulating baffle membranes, each membrane being located and moveable within a respective one of said baffle chambers, each membrane having an aperture substantially aligned with said aperture of said cryogenic chamber and being dimensioned for slidable engagement with said exterior dimension of said microtome arm.

2. A seal as recited in claim 1, wherein said seal container is thermally conductive.

3. A seal as recited in claim 2, further comprising, mean for heating a surface of said seal container.

4. A seal as recited in claim·2, wherein said seal container is aluminum.

5. A seal as recited in claim 2, wherein said seal container is copper.

6. A seal as recited in claim 2, wherein said seal container is brass.

7. A seal as recited in claim 1, wherein said baffle inserts are polystyrene.

8. A seal as recited in claim 1, wherein said baffle membranes are anti-static.

9. A seal as recited in claim 1, wherein said baffle membranes are mylar.

10. A seal as recited in claim 1, wherein said baffle membranes are mylar having an anti-static coating.

11. A seal as recited in claim 1, further comprising a thermally insulating baffle wall plug attached to said seal chamber, said plug having an external dimension suitable for press fitting said plug into said aperture of said cryogenic chamber.

12. A cryogenic ultramicrotome comprising:

a thermally insulating cryogenic chamber for maintaining an interior of said chamber at a low temperature relative to an exterior of said chamber, said chamber having at least one aperture between said interior and exterior;

a thermally insulating microtome arm extending through said chamber aperture and being moveable relative to said chamber; and a cryogenic seal attached to said chamber and surrounding said arm, said seal comprising:

a seal container attached to said cryogenic chamber and surrounding said arm;

a plurality of thermally insulating baffle inserts located within and substantially fixed relative to said seal container to form a plurality of baffle chambers between adjacent baffle inserts, each of said inserts having an aperture through which said arm passes without contact; and a plurality of baffle membranes located within said seal container between adjacent baffle inserts, each of said membranes having an aperture through which said arm passes in sliding contact.

13. A cryogenic ultramicrotome as recited in claim 12, wherein said seal container is thermally conductive.

14. A cryogenic ultramicrotome as recited in claim 13, further comprising a defrosting heater attached to an exterior of said seal container.

15. A cryogenic ultramicrotome as recited in claim 12, further comprising a wall plug fitted within said at least one aperture of said cryogenic chamber, and being attached to said cryogenic seal.

* * * * *

UNITED STATES PATENT AND TRADEMARK OFFICE
CERTIFICATE OF CORRECTION

PATENT NO. : 4,918,941

DATED : April 24, 1990

INVENTOR(S) : Herbert K. Hagler

It is certified that error appears in the above—identified patent and that said Letters Patent is hereby corrected as shown below:

Claim 1, column 3, line 65, change "reactively" to --relatively--.

Signed and Sealed this

Thirteenth Day of August, 1991

Attest:

HARRY F. MANBECK, JR.

*Attesting Officer*        *Commissioner of Patents and Trademarks*